United States Patent
Nevyas et al.

(10) Patent No.: US 7,513,621 B2
(45) Date of Patent: Apr. 7, 2009

(54) OPHTHALMIC OPERATIVE KERATOMETER WITH MOVABLE FIXATION/CENTRATION DEVICE

(76) Inventors: Herbert J. Nevyas, 231 Tower La., Narberth, PA (US) 19072; Anita Nevyas-Wallace, 231 Tower La., Narberth, PA (US) 19072

( * ) Notice: Subject to any disclaimer, the term of this patent is extended or adjusted under 35 U.S.C. 154(b) by 562 days.

(21) Appl. No.: 10/972,940

(22) Filed: Oct. 25, 2004

(65) Prior Publication Data
US 2005/0174537 A1  Aug. 11, 2005

Related U.S. Application Data

(60) Provisional application No. 60/514,251, filed on Oct. 24, 2003.

(51) Int. Cl.
*A61B 3/10* (2006.01)
*A61B 3/02* (2006.01)
(52) U.S. Cl. .................... 351/221; 351/212; 351/225
(58) Field of Classification Search ............. 351/212, 351/221, 246, 205, 224, 225, 211
See application file for complete search history.

(56) References Cited

U.S. PATENT DOCUMENTS

| | | | |
|---|---|---|---|
| 4,597,648 A * | 7/1986 | Feldon et al. ............... 351/212 |
| 4,685,140 A | 8/1987 | Mount, II |
| 4,772,115 A | 9/1988 | Gersten et al. |
| 4,786,163 A * | 11/1988 | Imamichi et al. ........... 351/212 |
| 4,863,260 A | 9/1989 | Gersten et al. |
| 4,902,123 A | 2/1990 | Yoder, Jr. |
| 4,978,213 A | 12/1990 | El Hage |
| 4,995,716 A | 2/1991 | Warnicki et al. |
| 5,009,498 A | 4/1991 | Gersten et al. |
| 5,018,850 A | 5/1991 | Gersten et al. |
| 5,062,702 A | 11/1991 | Bille |
| 5,106,183 A | 4/1992 | Yoder, Jr. |
| 5,159,361 A | 10/1992 | Cambier et al. |
| 5,227,818 A | 7/1993 | El Hage |
| 5,300,965 A | 4/1994 | Kitajima |
| 5,312,393 A | 5/1994 | Mastel |
| 5,416,539 A | 5/1995 | Gersten et al. |
| 5,418,582 A | 5/1995 | Van Saarloos |
| 5,526,072 A | 6/1996 | El Hage |
| 5,825,457 A * | 10/1998 | Luce et al. .................. 351/221 |
| 5,909,271 A | 6/1999 | Maus et al. |
| 2002/0049431 A1 | 4/2002 | Smith et al. |

* cited by examiner

*Primary Examiner*—William C Choi
*Assistant Examiner*—Jack Dinh

(57) ABSTRACT

Provided is an operative keratometer consisting of a built-in bright LED ring light, which uniquely provides immediate direct preoperative confirmation to the ophthalmologist of the proper meridian for astigmatic cuts and the most advantageous location of cataract incisions to minimize postoperative astigmatism. Also provided are methods for using the operative keratometer device to facilitate evaluation of the amount and direction of astigmatism in a patient. Further provided is a movable fixation/centration device and methods for its use to focus the operative keratometer, particularly for treating astigmatism, permitting the ophthalmologist to qualitatively assess both the amount and direction of the astigmatism; to more accurately conduct surgery near the pupil by providing a patient fixation point that permits the ophthalmologist to more precisely control movement of the patient's eye during an ophthalmic procedure; and to provide monocular centration of the patient's eye.

23 Claims, 2 Drawing Sheets

OPHTHALMIC OPERATIVE KERATOMETER WITH MOVABLE FIXATION/CENTRATION DEVICE

CROSS REFERENCE TO RELATED APPLICATIONS

This application claims priority to U.S. Provisional Application No. 60/514,251, filed Oct. 24, 2003, the content of which is herein incorporated in its entirety.

FIELD OF THE INVENTION

The present invention relates to an ophthalmic device, specifically a 360° fixation/centration device for a ring lighting system for a qualitative operative keratometer, and methods of use therefor.

BACKGROUND OF THE INVENTION

Refractive eye surgery to correct visual deficiencies and maladies includes, for example, lamellar corneal surgery, keratomileusis, epikeratophakia, cataract surgery, penetrating keratoplasty, conductive keratoplasty, corneal transplantation radial keratotomy, laser refractive keratectomy, and the like. Such therapeutic intervention involves incisions, punctures, sutures, etc. However, while ophthalmic microsurgery is often successfully performed, the results obtained can be subject to variation. In conductive keratoplasty, for example, a number of coagulation punctures are made into the cornea in order to change its curvature and correct refractive power. But, if the punctures are incorrectly placed, optimal vision will not result; and in some instances permanent distortions can result in corneal astigmatism, causing the vision of the patient to be worse than planned.

A keratometer is a standard instrument used for determining the curvature shape of the corneal surface of the eye. In use, the patient looks into the keratometer device, which then must be accurately positioned with respect to the patient's eye being examined along the line of view of the patient's eye (the optical axis between the pupil of the eye and the device). In some instances general centering of the device on the eye is sufficient, but in other cases exact centering of the device on the pupil or on the optical axis of the eye is critical to the success of the surgery.

The use of a circular illuminated ring on the keratometer causes a circular or elliptical reflection of the circular ring of light to appear on the patient's cornea. The reflection of the light by the tear film on the anterior surface of the cornea allows the ophthalmologist to more accurately view the surface contour of the eye, and target the center of the patient's eye during evaluation and refractive surgery. The reflection of the ring of light allows the ophthalmologist to measure the curvature of the cornea. Deviations of the cornea from sphericity cause bumps or indentations indicative of irregularities in the cornea to be present in the reflection. In an astigmatic eye the reflection of the circular ring of light appears elliptical to the ophthalmologist, and the degree of ellipticity is directly proportional to the amount of astigmatism present in the eye. The direction of the axis of the reflected ellipse corresponds to the direction of the astigmatism. Thus, the reflection provides information to the ophthalmologist regarding where incisions should be made and how much change is needed during the surgical intervention to correct the astigmatism in the patient's eye.

The keratometer's measurements relate to data actually measured at points peripheral to the apex of the patient's cornea, and as a result, the effectiveness and accuracy of the keratometer are directly dependent upon the accuracy of the positioning of the apparatus relative to the cornea. An accurate view of the eye, particularly for surgery near the pupil of the eye, depends directly upon the centering of the device, since misalignment of the equipment can result in skewed measurements and inaccuracies.

In general, the microsurgery is performed under a binocular microscope, which combines the two images, one produced by each ocular to each of the surgeon's eyes, into one image with depth perception. Parallax is the difference between two images. When a single image is viewed with both of an ophthalmologist's two eyes, each eye views the image from a slightly different angle because of the spacing between the two eyes. Each eye, therefore, has its own line of sight to the object being viewed, and when combined, a parallax occurs. By comparison, in a monocular view, i.e., using only one eye to view a two-dimensional image, no parallax occurs. However, the eye is 3-dimensional, not 2-dimensional. Consequently, the cornea at the center of the eye covering the pupil is not flat, but is raised 3-5 mm over the pupil, creating its own parallax when viewed binocularly. This error can be eliminated when the center of the pupil and the apex of the cornea are in alignment within the monocular line of sight of the ophthalmologist.

Improvements in the accuracy of the corneal visualization by ophthalmologists and microsurgeons will improve their ability to perform refractive surgery. Accordingly, a need continues to exist for a simple and precise method for focusing an operative keratometer, particularly in treating astigmatism, to permit the ophthalmologist to 1) qualitatively assess both the amount and direction of the astigmatism, 2) more accurately place incisions, punctures, sutures or other types of surgical intervention by providing a movable fixation point that provides direction for the patient to focus the subject eye, thereby placing the eye at a more convenient position for the ophthalmologist during surgery, and also to evaluate the effect of each incision, puncture, suture, etc. (postoperative compared with preoperative, or during surgery), and 3) to provide monocular centration of the optical axis and/or the pupil as needed, particularly for surgery near the pupil of the eye.

SUMMARY OF THE INVENTION

The present invention is directed to improvements in the art of keratometry to meet the identified needs, and more particularly to (1) an improved fixation device and method for its use, and (2) an improved centration device and method for its use. Additional improvements and systems comprising them will be further provided.

One objective of the present invention is to provide a central centration point for viewing of the patient's eye without substantially blocking, reducing and/or distorting the reflected light traveling back up through the microscope to the ophthalmologist. Accordingly, the device uses the smallest light source possible to accomplish these purposes.

Similarly, it is another object to provide a movable device for improved monocular centration of a fixation/centration light attached to a surgical binocular microscope, wherein the device comprises: a directionally movable light source within a ring-shaped casing, wherein the casing has an ophthalmologist-facing top side, and a patient-facing lower side, both of which are open or transparent to expose the light source within, wherein the casing creates a minimal footprint in line of vision of the ophthalmologist viewing a patient's eye (Z-axis), such that light is projected as a single focused beam of light on, or parallel to, the Z-axis by the light source from within the casing, simultaneously through both the upper and lower sides of the casing ring.

It is an additional object to provide a method of using the movable fixation/centration device for both monocular centration and patient fixation. Accordingly light is projected simultaneously in both directions on, or parallel to the Z-axis, thereby permitting simultaneous viewing of the projected light by both ophthalmologist and patient.

In yet another object a method is provided for using the movable fixation/centration device for monocular centration by the ophthalmologist, who views the projected light projected onto the patient's eye through just one ocular of the two provided on a binocular microscope, until monocular center is located. Once the device has been monocularly centered, the ophthalmologist can resume binocular viewing of the field.

In still another object, a method is provided for using the movable fixation/centration device as a patient fixation device, in which case the light is projected toward the patient, and the patient is instructed to fixate upon the light, and to remain focused on the light if it is moved by the ophthalmologist, thereby controlling the eye movement of the patient during an ophthalmic procedure.

In a further object, there is provided an improved lighting system for an ophthalmic keratometer, comprising: a ring light for said ophthalmic keratometer, to which ring light is rotatably and radially movably-attached the directionally movable light source within the ring-shaped casing as described above, such that light is projected as a focused beam on, or parallel to, the Z-axis by the light source from within the casing, simultaneously through both the upper and lower sides of the casing ring; and a means for circumferentially rotating the light source on the X,Y-axes around the ring light, and for radially moving the light source on the X,Y-axes within the ring light to permit centration of the light source with regard to the patient's eye.

In yet another object, there is provided an ophthalmic microscope system having a self-contained improved lighting system for an ophthalmic keratometer, comprising: a binocular microscope adapted for ophthalmic procedures; an ophthalmic keratometer; a ring light for said ophthalmic keratometer, to which ring light is circumferentially rotatably movably-attached and radially movably-attached the directionally movable light source within the ring-shaped casing, such that light is projected as a focused beam on, or parallel to, the Z-axis by the light source from within the casing, simultaneously through both the upper and lower sides of the casing ring; and a means for rotating the light source on the X,Y-axes around the ring light, and for radially moving the light source on the X,Y-axes within the ring light to permit centration of the light source with regard to the patient's eye.

In a further object there is provided an operative keratometer consisting of a built-in bright LED ring light comprising a series of evenly spaced individual LED lights around the circumference of the ring, each of which projects a point of light toward the patient's eye, thereby generating a dotted pattern of light on the patient's eye, which in turn is reflected back to the ophthalmologist. Also provided is a unique method for using the defined ring light by an ophthalmologist to provide immediate, direct operative confirmation of the proper meridian for surgical intervention to correct astigmatism, as well as to compare the surgical steps taken during ophthalmic surgery to allow the surgeon to determine the extent and location of the next surgical step. Additional unique advantages will been seen from the use of the defined ring light that projects a pattern of individual points of light onto the eye of the patient, as well as from combining that unique ring light with the movable fixation/centration device described herein.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended drawings. It should be understood, however, that the invention is not limited to the precise arrangements and instrumentalities shown.

DETAILED DESCRIPTION OF CERTAIN PREFERRED EMBODIMENTS

Figure 1:
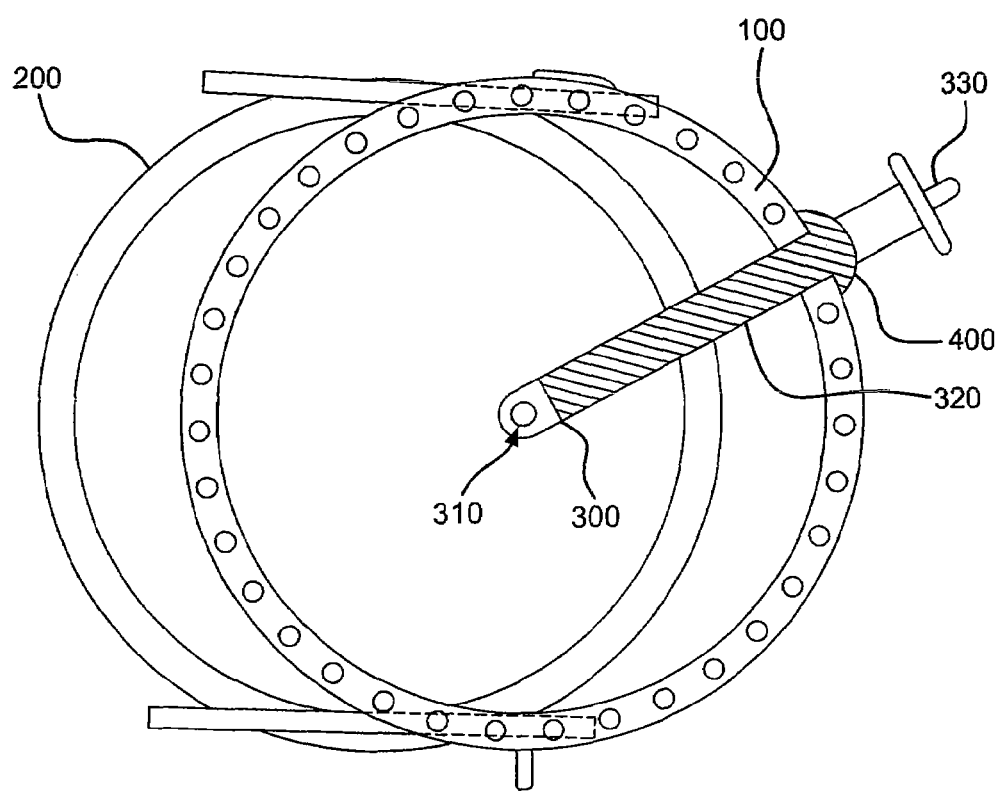
FIG. 1 is a bottom view (as would be viewed from the point of view of the patient during use) of a preferred embodiment of the invention, showing the lighting device in place suspended from the outer edge of ring light 100, which is further supported by ring light attachment ring 200.

The present invention provides a means for improving ophthalmic evaluation and microsurgery, more specifically a means for improving keratometer ring illumination systems. Further provided are methods of advantageously using the a movable fixation/centration device to focus an operative keratometer, particularly for treating astigmatism, permitting the ophthalmologist 1) to qualitatively assess both the amount and direction of the astigmatism, 2) to more accurately place incisions by providing a fixation point that provides direction for the patient to focus the subject eye, thereby placing the eye into a more convenient position for the ophthalmologist during surgery, and also to permit the ophthalmologist to evaluate the effect of each incision, puncture, suture or surgical procedure during eye surgery, and 3) to provide monocular centration of the optical axis and/or the patient's pupil as needed, particularly for surgical procedures near the pupil of the eye.

This present device is adapted for use in association with an optical instrument, such as a binocular or stereoscopic microscope. Accordingly, recognizing that other vision enhancing instruments may be involved, the specification will simply refer to all such optical instruments employed for the observation of the zone of intervention in surgery and microsurgery as a "microscope."

The present invention is adapted for mounting to a circular illuminating ring system attached to a conventional binocular or stereoscopic microscope in accordance with devices previously known in the art, for example, the Nevyas Operative Keratometer/360° Fixation Device produced commercially by Varitronics, Inc., (Broomall, Pa.) or U.S. Pat. No. 5,312, 393, herein incorporated by reference. As a result, the microscope, attachment of the ring housing to the microscope, and means for transmitting light from the lighted ring is not further described herein, but will be understood by one of ordinary skill in the art. Solid ring lights in the prior art, include ring-shaped halogen lights, fluorescent lights, high-intensity light-emitting diodes (LEDs), and ring shaped polished cavities into which light is directed through a fiber optic bundle, have been described, e.g., U.S. Pat. Nos. 4,685,140; 4,772,115; 4,863,260; 4,978,213; 4,995,716; 4,902,123; 5,009,498; 5,018,850; 5,062,702; 5,106,183; 5,159,361; 5,227,818, 5,312,393; 5,300,965; 5,416,539; 5,418,582 and 5,526,072, the entire contents of which are incorporated herein by reference.

In a preferred embodiment, the instrument includes an operative keratometer consisting of a built-in bright LED ring light, which in contrast to the prior art, provides immediate direct preoperative confirmation of the proper meridian for astigmatic cuts and the most advantageous location of the cataract incision to minimize postoperative astigmatism. The inventors have discovered certain advantages that result from projecting a pattern of light points, as opposed to a solid, uninterrupted ring of light from the lighted ring. This is accomplished by providing a series of evenly spaced individual LED lights around the circumference of the ring, each of which projects points of light toward the patient's eye, thereby generating a "dotted" pattern of light on the patient's eye, which in turn is reflected back to the ophthalmologist.

The regular spacing of the light points in the LED ring light provides certain advantages to the ophthalmologist, particularly in methods for treating astigmatism, that were not previously recognized when the prior art solid lighted rings were used. The regular spacing of the lights provide clues to the ophthalmologist regarding the direction of the patient's astigmatism. As noted above, in an astigmatic eye, the reflected pattern of light from the projected circle of light from the ring light is an ellipse. But, when the projected pattern comprises a circle of evenly spaced individual lights, the elliptical reflection from the astigmatic eye causes the dots to appear closer together along the short axis, and further apart along the long axis of the ellipse. This not only facilitates evaluation of the amount and direction of the astigmatism, it also assists the ophthalmologist in visualizing the keratometric result of each incision, puncture, suture or the like during surgery to determine the placement and degree of the next incision until the reflection of the keratometer ring has become circular.

Although any color of light, or even white light is acceptable, for this purpose so long as the lights are evenly spaced, the use of red light projected from the ring light has been found to provide improved reflectivity off of the cornea. Conventional filters, baffles or diffusers could also be added to the individual light sources on the present ring light to alter the projected pattern, from one of evenly spaced dots, to an apparently solid or nearly solid ring of light, or to create defined light segments.

In yet another preferred embodiment of the present invention the ring light is combined with a directionally movable fixation light. As will be described in greater detail below, the fixation light is perfectly centered within the keratotomy ring when the fixation light device of the present invention it is pushed radially to its maximally inward position placing the movable light at the precise center of the ring light from any location on around the circumference of the ring. It is this unique combination of the movable fixation light and keratometer ring (together forming a "fixating keratoscope" or "fixating keratometer") that allows the ophthalmologist to perfect surgery to correct astigmatism by aliquots. In practice, the surgeon performs a certain amount of surgery, visualizes the keratometric result, and then performs further surgery until the keratometer ring appears circular when reflected from the patient's eye.

The movable fixation light is aligned with respect to orthogonal axes X, Y and Z. The Z-axis defines the line of sight, or "optical axis" between the ophthalmologist and the center of the patient's eye, effectively defining the distance between the two. When monocularly centered, the optical axis defines the line between the macula of the patient and the macula of the ophthalmologist. The X- and Y-axes are on the same plane, but perpendicular to the Z-axis, thereby permitting alignment of the device. The X-axis moves the device radially left and right from its point of origin; the Y-axis moves the device radially forward and backward from the point of origin.

In a preferred embodiment of the invention, a single beam or fixation point of light is provided within the embodied ring light, oriented between the objective lens of the microsurgery microscope and the patient's eye being examined, projecting light from the light source in both directions on, or parallel to, the Z-axis. The ring light alone, or the ring light in combination with the movable fixation light, does not interfere with the existing illumination system on most microscopes, and can be readily added by known means. In a further embodiment, the movable fixation light is of adjustable intensity to provide safe, controlled lighting.

The present device for providing the movable fixation light offers an advantageous alternative to the prior art, wherein the fixation light was not movable. Because the movable fixation light is visible to the patient, it advantageously serves as a patient alignment device in a variety of corneal procedures. Initially the fixation light is generally centered within the ring light and acts as a general "fixation point" upon which the patient is instructed to focus, which was the sole function served by fixation lights in the prior art. However, because the fixation light of the preferred embodiment can be moved to any point within the ring light, during examination or surgery the ophthalmologist can move the light and thereby direct the patient to move his/her focus to the new position of the light. This moves the patient's eye exactly in a particular direction relative to the previous point (left, right, up down, etc) as directed.

This allows the ophthalmologist to position the patient's eye into better location, not only at the start of the surgery, but more importantly, as needed during surgery. For example, by instructing the patient to move the focus of eye off center to an exact location, the ophthalmologist can avoid interference by obstructions, such as the patient's nose, to more clearly view the field for making certain incisions. This capability is particularly useful when the surgeon needs to fixate the eye upward or downward, left or right, for a more convenient surgical approach, for example, to the 12 o'clock position or to the side to allow the surgeon optimal visualization, as with limbal astigmatic keratotomy incisions.

Since fixation lights in the prior art were not movable, the patient was only given verbal directions to move the eye, such as up or down. But now, the present invention provides the ophthalmologist with much greater control over how far the patient moves the eye, and in which direction. In addition, the movable fixation light allows the patient to concentrate on the light, which may relieve some of the patient's anxiety. But more importantly, the movable fixation light permits the patient to assist the ophthalmologist by moving the eye into the exactly the most advantageous position during surgery, and then fixate on the new position of the light until told to move the eye again.

As a result, the present invention helps keep the eye steady by giving the patient a comfortable fixation point, while at the same time it protects the fovea from damage by giving the patient a non-dazzling target, as compared with focussing on the intensely bright microscope light which can actually damage the eye. Thus, the patient is less likely to move the eye unintentionally during surgery, and is protected from injury by the light itself. In an alternative embodiment, the fixation light blinks at a steady, non-irritating rate to help catch the patient's attention and to assist the patient in concentrating and focusing on the fixation light.

Therefore, the improved device and systems comprising the improved device, as well as methods of using the present invention, offer significant advantages over previous visualization devices for use in ophthalmic diagnostic procedures and microsurgery. Movement of the movable light source providing the fixation light of the present invention is well suited to the natural hand-eye coordination capabilities of the ophthalmologist using the device, which is particularly important when the fixation light is moved during surgery. The device is also compatible with, and easily integrated into, existing commercial microscopes adapted for ophthalmic purposes. Moreover, because the movable light source is so small, it does not obstruct, block, reduce and/or distort the ophthalmologist's view of the surgical field. This target can also achieve good fixation for "no forceps" keratotomy surgery.

Advantageously, the light source and projected beam of light provided in the present invention serves yet another purpose. In addition to being a fixation light, it also offers a centration point for the ophthalmologist, and advantageously it offers both capabilities simultaneously. Others have used a light beam from a much larger box, such as earlier versions of a fixation light produced by Varitronics, Inc., as compared with that which is used in the present invention. See, for example, U.S. Pat. Nos. 4,772,115 and 5,312,393.

Therefore, in an addition embodiment, the centered light of the present invention also provides the ophthalmologist with a "centration point" to overcome parallax problems associated with binocular vision as described above. For general ophthalmic surgery, general centration of the device may be adequate, e.g., as provided when the movable light source of the present invention is set at the mechanical center of the ring light. However, for other procedures, such as for conductive keroplasty, when incisions, punctures or other surgical procedures must be made very close to the pupil and errors could permanently damage the patient's vision, centration of the device on the optical axis is essential.

In this preferred embodiment, the ophthalmologist achieves monocular centration of the patient's eye, by viewing the subject field through just one ocular of the two provided. This accomplished perhaps by closing one eye that the ophthalmologist is not using to view the field (the non-selected eye), or by occluding the vision in the non selected eye with a paddle, patch or other device. By viewing the field through only one ocular (using the selected eye), a parallax-free view is provided that the ophthalmologist would see if viewing the field through a monocular microscope. Accordingly, this embodiment is advantageous for procedures that require dead-center viewing (macula to macula) that is not distorted by parallax.

This view permits the ophthalmologist to locate the monocular center and place the fixation device point of light at that point. The device is, then, said to be "monocularly centered." And in fact, by this use of the invention, the binocular microscope serves as a monocular marking scope, without the need to move the patient or the field to accomplish monocular centering of the device. Once the device has been monocularly centered, it will remain in that position, and until it is moved, the ophthalmologist can resume using both eyes to view the field of the patient's eye.

In a particularly preferred embodiment, the movable light is transmitted from an LED device to the eye of the patient and to the ophthalmologist simultaneously, although as will be explained, the light transmitted to the ophthalmologist is less bright than that which is transmitted to the patient as the fixation light. As a result, in contrast to the prior art devices, the movable light of the present invention is, therefore, visible to both the patient and to the ophthalmologist (together referred to as a "fixation/centration" device).

The fixation points within the ring illumination systems of the prior art, have not only been immobile, they have previously been visible only to the patient. See, e.g., red dot provided in U.S. Pat. Nos. 4,772,115. Ophthalmologists, on the other hand, in the prior art, saw only a small area of black (absence of light) at the approximate center of the ring, which was, if not impossible, at least very difficult to center when accurate centration was critical.

Consequently, combining the capability of transmitting a movable fixation point and a monocular centration device into a single miniaturized unit, results in an efficiency of space, efficiency and effectiveness. Light source 100 is much smaller than previously possible, requiring a significantly smaller footprint within the ophthalmologist's line of sight, as compared with capabilities in the prior art. Advantageously, by the methods of the present invention, the ophthalmologist's view of the patient's pupil is no longer obscured by the larger footprint required by the prior art fixation devices. Accordingly, by using the present device and methods, ophthalmic procedures are more accurately and reliably performed.

Any suitable light source may be used for the center light. For example, typical point sources include, for example, light emitting diodes ("LED"), and fiber optic bundles to bring light from an outside source through a prism and emit it at the central location towards the surgery field. However, an LED light is preferred in the disclosed embodiments. Of course, to permit either the patient and/or the ophthalmologist to view the center point of light for an extended period of time, the optimal intensity of the light must be such that the viewer (i.e., the patient or ophthalmologist) is not blinded, dazzled or distracted by the light. Thus, while LED lights are commercially available in a range of wavelengths and intensities, the preferred light of this invention is further selected to be comfortably viewed by both the patient and the ophthalmologist for extended periods of time without causing eye-strain.

In an alternative embodiment, a movable click-stop may be added to the ring to facilitate centering of the device within the ring, or to mark certain predetermined positions on the radial path of the device around the ring light support.

Reference will now be made in detail to preferred embodiments of the present invention, examples of which are illustrated in the accompanying drawings.

As shown in FIG. 1, a ring light 100 is attached to the optical viewing head by attachment ring support 200. Further description of the optical head and attachment of ring light 100 is beyond the scope of this invention and will rely on prior art devices of the types previously referenced in the specification.

Suspended below (meaning on the patient-side of) ring light 100, a movable fixation/centration light is attached to the outer rim of ring light 100. The light has a casing 300 that is disc-like or doughnut-shaped. Casing 300 has a top side directed towards the ophthalmologist, and a lower side directed toward the patient's eye, and in use the light is visible on both sides. Casing 300, therefore, surrounds on all sides, light source 310 (preferably LED light), but casing 300 does not obscure light on the top or bottom sides. Thus, the light is luminous and exposed during use, projecting light in both directions, essentially parallel to line of sight Z, i.e., to the side facing the patient (from its lower side), and simultaneously to the opposite side facing the ophthalmologist (from its upper side). The sides of casing 300 surrounding light source 310 are opaque to prevent random light from escaping along the X,Y-axes.

Casing 300 is in one embodiment open in the top and bottom sides, and light source 310 actually forms the top and bottom sides of casing 300. In an alternative embodiment, the top and bottom sides of casing 300 comprise a transparent material, to permit light from light source 310 to be projected there-through on, or parallel to, the Z-axis. The light transmitted to the ophthalmologist from the top side of the light source is less bright than that transmitted to the patient from the bottom side of the light source. Generally, the difference in brightness is achieved if the opening in the top side of casing 300 is smaller than the opening used to transmit light from the bottom side. As a result, the transmitted light is not so bright to the ophthalmologist that it cannot be ignored when not being used by the ophthalmologist, and it is not so bright as to be distracting or annoying.

Casing 300 may be made of any suitable material for use in encasing a light source, but optimally an inexpensive, lightweight material, such as a moldable plastic is preferred. Similarly light source 310 is similarly formed from an inexpensive, light-weight material, such as a moldable or machinable plastic.

Casing 300 is minimal in size, not exceeding 5 mm in diameter, preferably less than 4.5 mm in diameter, more preferably less than 4.0 mm in diameter, more preferably less than 3.5 mm in diameter and most preferably less than 3.0 mm in diameter, to minimize blocking the line of vision of the ophthalmologist. In a further preferred embodiment casing 300 is less than 2.5 mm in diameter. In each case, light source 310 is of a size to fit within casing 300.

Casing 300 is mounted to radial arm 320, comprising the electrical wiring circuit needed to illuminate light 310. Radial arm 320 is on the same plane as casing 300 and of a length that extends (with casing 300 and light source 310 attached) from the precise center of ring light 100 (when radial arm 320 is pushed to its fully extended radial position on the X,Y-axes), to a point on the circumference of ring light 100 (when radial arm 320 is radially retracted to its fully retracted position on the X,Y-axes). Radial arm 320 is in a fixed and immovable connection with casing 300, but it is circumference-rotatably attached (able to move circumferentially around the circumference of the ring, but not moving out of the horizontal plane suspended beneath ring 100) to ring light 100 by attachment point 400. Radial arm 320 extends to the outside of ring light 100, ending in a handle region 330 to permit the ophthalmologist to move casing 100 (at the casing-end of the radial arm 320) in the X,Y-axes within the plane of the ring light.

Handle 330 can be of any size or shape that is convenient and permits the ophthalmologist to move the light source 310 within ring light 100, without diminishing the effectiveness of the present invention to simultaneously project the fixation light and centration light. Handle 320 is replaceable and sterilizable. Similarly, covers for the switches that control whether the light is on, off or blinking are also removable and sterilizable.

Figure 2:
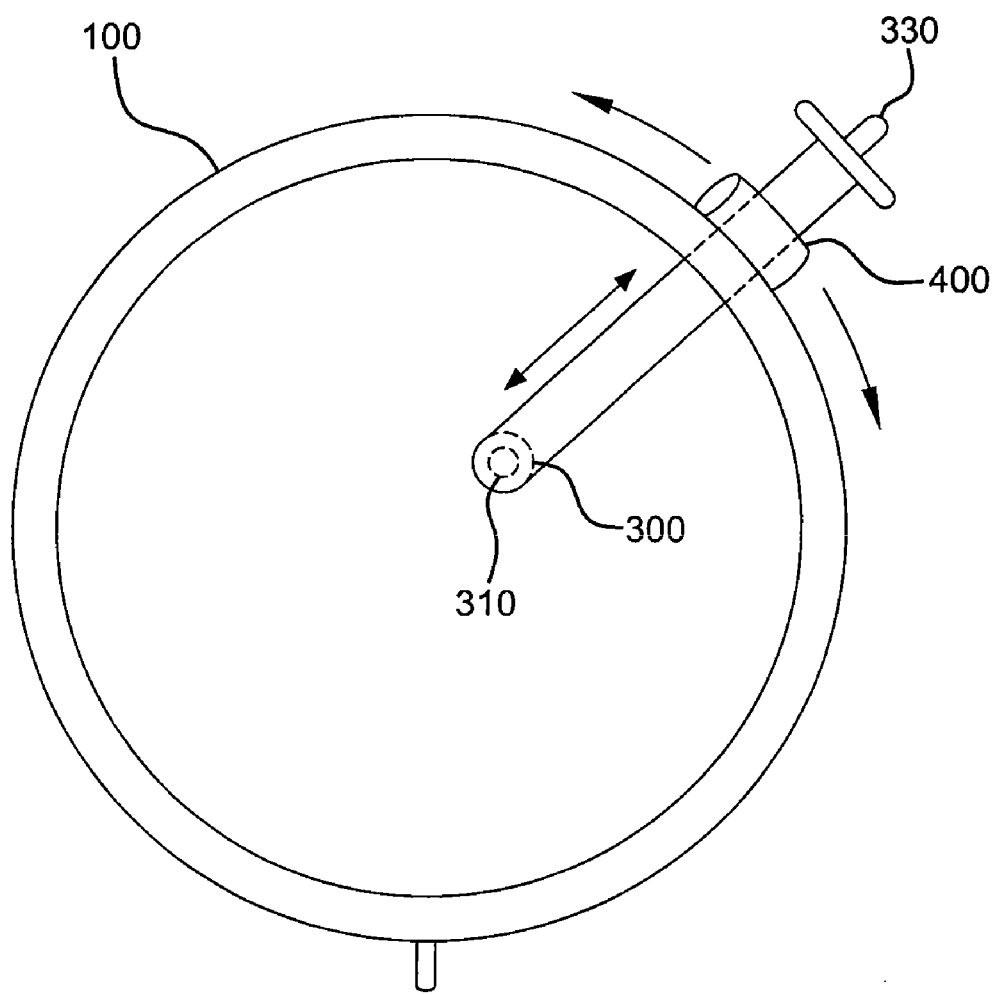
FIG. 2 is a top view (as would be viewed from the point of view of the ophthalmologist during use) of a preferred embodiment showing the circumferential movability (around the circumference of ring light 100, and radial movability of the lighting device in or out along a radius of ring light 100, whereas each movement of the movable lighting device remains within the same horizontal plane.

As shown in FIG. 2, casing 300, and light source 310 contained therein, are movably attached to ring light 100, such that at attachment point 400, casing 300 and light source 310 contained therein, can be moved to any point on ring light 100. Thus, casing 300, and the light source 310 contained therein can be moved 360° around ring light 100, while remaining on the same X,Y-plane, essentially perpendicular to the Z-axis. In a preferred embodiment, movement of casing unit 300 is accomplished by sliding point of attachment 400 circumferentially around ring light 100, but remaining on the same horizontal plane suspended beneath ring light 100. In the alternative, attachment point 400 can be physically releasable and reattachable, permitting independent movement of casing unit 300, but that would prove cumbersome, and is not preferred. However, the release capability is useful for replacing the light source or other maintenance of the device, or to remove it when not needed in ring light 100.

In addition to the ability to radially slide radial arm 320 attached to ring light 100 at attachment point 400 around ring light 100, the present device provides the additional ability for the ophthalmologist to move radial arm 320 radially at attachment point 400 on ring light 100. The movement is possible because attachment point 400 not only permits the attachment point itself and the radial arm 320 to slidably rotate circumferentially around ring light 100 on the plane of ring light 100, while the projected light remains projected on, or parallel to, the Z-axis, attachment point 400 also permits radial arm 320 to easily slide radially on the radial X,Y-axes, essentially forming radii of ring light 100, extending from the center of ring light 100 radially to attachment point 400.

As an example, if handle 330 were effectively in the 3 o'clock position on ring light 100 relative to the ophthalmologist, the ophthalmologist could slide handle 330 and the radial arm 320 attached thereto to any point around ring light 100 on the X,Y plane. In addition, he/she could push handle 330 (and radial arm 320 attached thereto) radially centerward on the X,Y-axes, to the center point of ring light 100, or pull handle 330 (and radial arm 320 attached thereto) toward attachment point 400 on ring light 100, while remaining within the X,Y plane and at the 3 o'clock position. Or, the device could be moved both circumferentially and radially. When all of the movement capabilities are combined, the ophthalmologist can quickly and accurately center light source 310 to any point in ring light 100, without causing the patient to move. The process can be repeated or light source 310 relocated at any time during the ophthalmic procedure so that accurate measurements and determinations and re-positioning of the eye may be made in a fast, accurate, and consistent manner.

Throughout the foregoing specification, the terms operator, surgeon, user, persons, individuals or other similar terms are used interchangeably since each may benefit from the present invention. However, the term "ophthalmologist" is the preferred term used herein to refer to all such users of the invention, but such term is intended to include all such individuals who may benefit from the use of the present device, even if not medically trained as an ophthalmologist. "Patient," of course, refers to the individual on whom the present device is being used, and while primarily intended to mean human patients, is also intended to include other animals.

It should also be understood that the system of the invention is useful to the ophthalmologist as a diagnostic and analytical tool, aside from its uses in actual surgery. The system permits highly stabilized imaging of the patient's tissue, particularly the ocular tissue, to an extent not achievable by instruments in the prior art. Thus, the present invention provides the ophthalmologist with a significantly improved tool for the evaluation and treatment of a patient's condition, as well as for refractive surgery.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

We claim:

1. A movable device for improved monocular centration of a fixation light attached to a surgical binocular microscope, said device comprising: a directionally movable light source within a ring-shaped casing, wherein the casing has an ophthalmologist-facing top side, and a patient-facing lower side, both of which are open or transparent to expose the light source within, wherein the casing creates a minimal footprint in line of vision of the ophthalmologist viewing a patient's eye, designated the Z-axis, such that light is projected as a single focused beam of light on, or parallel to, the Z-axis by the light source from within the casing, simultaneously through both the upper and lower sides of the casing ring.

2. The device of claim 1, wherein the light source comprises light emitting diodes (LED) or fiber optic bundle to bring light from an outside source.

3. The device of claim 2, wherein the light source is an LED.

4. The device of claim 1, where the projected light is white or any visible color.

5. The device of claim 4, wherein the projected light is red or orange.

6. The device of claim 1, wherein the brightness of the light projected to the ophthalmologist from the top side is less than the light projected to the patient from the lower side.

7. The device of claim 1, wherein intensity of the projected light is controllably variable.

8. A method of using the device of claim 1, said method comprising both monocular centration and patient fixation, said method comprising projecting light simultaneously in both directions on, or parallel to the Z-axis, thereby permitting simultaneous viewing of the projected light by both ophthalmologist and patient.

9. A method of using the device of claim 8 for monocular centration, comprising:
projecting light through the upper side of the casing to the ophthalmologist; then viewing by the ophthalmologist of the patient's eye through just one ocular of the two provided, until locating monocular center; and placing the light source at the monocular center.

10. The method of claim 9, further comprising resuming binocular viewing by the ophthalmologist after monocular centration of the device.

11. A method of using the device of claim 8 as a patient fixation device, comprising:
projecting the focused beam of light through the lower side of the casing to the patient; then fixating the view of the patient on the light, thereby precisely controlling eye movement of the patient during an ophthalmic procedure.

12. An improved lighting system for an ophthalmic keratometer, said system comprising: a ring light for said ophthalmic keratometer, to which ring light is rotatably and radially movably-attached the directionally movable light source within the ring-shaped casing in accordance with claim 1, such that light is projected as a light beam on, or parallel to, the Z-axis by the light source from within the casing, simultaneously through both the upper and lower sides of the casing ring; and a means for rotating the light source on the X,Y-axes circumferentially around the ring light, and for radially moving the light source on the X,Y-axes within the perimeter of the ring light to permit centration of the light source with regard to the patient's eye.

13. The system of claim 12, further comprising a means for controlling the intensity of the beam of light projected from the light source.

14. The system of claim 12, wherein the light source comprises a light emitting diodes (LED) or fiber optic bundle to bring light from an outside source.

15. The device of claim 14, wherein the light source is an LED.

16. The device of claim 12, where the projected light is white or any visible color.

17. The device of claim 16, wherein the projected light is red or orange.

18. An ophthalmic microscope system having a self-contained improved lighting system for an ophthalmic keratometer, comprising: a binocular microscope adapted for ophthalmic procedures; an ophthalmic keratometer; a ring light for said ophthalmic keratometer in accordance with claim 1, to which ring light is circumferentially rotatably movably attached and radially movably-attached the directionally-movable light source within the ring-shaped casing, such that light is projected as a light beam on, or parallel to, the Z-axis by the light source from within the casing, simultaneously through both the upper and lower sides of the casing ring;
and a means for rotating the light source on the X,Y-axes around the ring light, and for radially moving the light source on the X,Y-axes within the ring light to permit centration of the light source with regard to the patient's eye.

19. The system of claim 18, further comprising a means for controlling the intensity of the beam of light projected from the light source.

20. The system of claim 18, wherein the light source comprises a light emitting diodes (LED) or fiber optic bundle to bring light from an outside source.

21. The device of claim 20, wherein the light source is an LED.

22. The device of claim 18, where the projected light is white or any visible color.

23. The device of claim 22, wherein the projected light is red or orange.

* * * * *